(12) United States Patent  
Compo et al.

(10) Patent No.: US 12,296,055 B2  
(45) Date of Patent: May 13, 2025

(54) POUCH WITH BREAKABLE SEAL

(71) Applicant: Veltek Associates, Inc., Malvern, PA (US)

(72) Inventors: Mark J. Compo, Doylestown, PA (US); Michael Balestri, Mechanicsville, VA (US)

(73) Assignee: Veltek Associates, Inc., Malvern, PA (US)

( * ) Notice: Subject to any disclaimer, the term of this patent is extended or adjusted under 35 U.S.C. 154(b) by 526 days.

(21) Appl. No.: 16/572,064

(22) Filed: Sep. 16, 2019

(65) Prior Publication Data

US 2020/0085982 A1 Mar. 19, 2020

Related U.S. Application Data

(60) Provisional application No. 62/732,360, filed on Sep. 17, 2018.

(51) Int. Cl.  
*A61L 2/00* (2006.01)

(52) U.S. Cl.  
CPC ....... *A61L 2/0088* (2013.01); *A61L 2202/123* (2013.01); *A61L 2202/181* (2013.01); *A61L 2202/21* (2013.01); *A61L 2202/23* (2013.01)

(58) Field of Classification Search  
CPC .............. A61L 2/0088; A61L 2202/123; A61L 2202/181; A61L 2202/21; A61L 2202/23; A61L 2/18; A61L 2202/17; A61L 2202/25; A61L 2101/20; B65D 81/3261; A47L 13/17  
See application file for complete search history.

(56) References Cited

U.S. PATENT DOCUMENTS

| | | | |
|---|---|---|---|
| 3,036,616 | A | 5/1962 | Allen |
| 3,625,351 | A | 12/1971 | Eisenberg |
| 3,930,041 | A | 12/1975 | Komatsu et al. |
| 5,200,200 | A | 4/1993 | Veech |
| 5,616,337 | A | 4/1997 | Kasianovitz et al. |
| 5,811,113 | A | 9/1998 | Dorr et al. |
| 6,062,381 | A | 5/2000 | Paley |

(Continued)

FOREIGN PATENT DOCUMENTS

| | | |
|---|---|---|
| CN | 1897994 A | 1/2007 |
| CN | 101223912 A | 7/2008 |

(Continued)

OTHER PUBLICATIONS

Curbell Plastics, LDPE Properties (Year: 2017).*

(Continued)

*Primary Examiner* — Sean E Conley  
*Assistant Examiner* — Brendan A Hensel  
(74) *Attorney, Agent, or Firm* — Blank Rome LLP

(57) ABSTRACT

A wipe kit includes a pouch having a first compartment with a one-way valve coupled to an end thereof, a second compartment, and a frangible seal between the first and second compartments. The first compartment receives a liquid through the one-way valve and the second compartment contains a dry wipe. The frangible seal can be broken to permit liquid to flow from the first compartment onto the wipe in the second compartment. The deactivation wipe kit may be used in a clean room to deactivate most hazardous drugs on a work surface.

23 Claims, 5 Drawing Sheets

(56) References Cited

U.S. PATENT DOCUMENTS

| | | |
|---|---|---|
| 6,123,900 A | 9/2000 | Vellutato |
| 6,231,559 B1 | 5/2001 | Loretti |
| 6,289,889 B1 | 9/2001 | Bell et al. |
| 6,387,384 B1 * | 5/2002 | Probert ............... A61L 2/0088 |
| | | 424/661 |
| 7,066,354 B2 | 6/2006 | Stank et al. |
| 7,357,248 B2 | 4/2008 | Sivakumar et al. |
| D601,038 S | 9/2009 | Middleton-Schluter |
| 8,080,216 B2 | 12/2011 | Green et al. |
| 8,118,158 B2 | 2/2012 | Igota et al. |
| 8,162,137 B2 | 4/2012 | Vellutato, Jr. et al. |
| 8,449,186 B2 | 5/2013 | Bray |
| 9,108,208 B2 | 8/2015 | Vellutato, Jr. et al. |
| 9,334,098 B1 | 5/2016 | Hughes |
| 9,440,779 B1 * | 9/2016 | Hach ................ B65D 81/3261 |
| D783,416 S | 4/2017 | Bray |
| D784,158 S | 4/2017 | Bray |
| D819,454 S | 6/2018 | Bray |
| D820,687 S | 6/2018 | Bray |
| 10,131,474 B2 | 11/2018 | Py |
| 10,138,448 B2 | 11/2018 | Compo et al. |
| 10,745,656 B2 | 8/2020 | Compo |
| 11,111,466 B2 | 9/2021 | Compo |
| 11,420,170 B2 | 8/2022 | Pisacane |
| 2002/0130138 A1 | 9/2002 | Crozet et al. |
| 2003/0009989 A1 | 1/2003 | Knoerzer et al. |
| 2005/0221113 A1 | 10/2005 | Bitowft et al. |
| 2006/0124476 A1 * | 6/2006 | Sivakumar ............. A47L 13/17 |
| | | 206/207 |
| 2008/0255535 A1 | 10/2008 | Yoshikawa |
| 2009/0238502 A1 | 9/2009 | Bhattacharjee et al. |
| 2009/0297069 A1 | 12/2009 | Bray |
| 2010/0142862 A1 | 6/2010 | Sam |
| 2010/0273622 A1 | 10/2010 | Vonderhaar |
| 2010/0314267 A1 | 12/2010 | Green et al. |
| 2011/0084098 A1 * | 4/2011 | Py ..................... B65D 83/0061 |
| | | 137/511 |
| 2011/0210120 A1 | 9/2011 | Nevo |
| 2011/0280501 A1 | 11/2011 | Brauer et al. |
| 2012/0066850 A1 | 3/2012 | Pisacane et al. |
| 2012/0269459 A1 | 10/2012 | Howes |
| 2013/0095058 A1 | 4/2013 | Bylemans et al. |
| 2013/0126370 A1 | 5/2013 | DiLiberto et al. |
| 2013/0153448 A1 | 6/2013 | Yoshikawa |
| 2013/0236128 A1 | 9/2013 | Bray |
| 2014/0033655 A1 | 2/2014 | Stanley et al. |
| 2014/0034081 A1 * | 2/2014 | Asano ................. A47L 13/258 |
| | | 15/104.93 |
| 2014/0143857 A1 | 5/2014 | Maim |
| 2014/0215969 A1 | 8/2014 | Parthon et al. |
| 2015/0101287 A1 | 4/2015 | Vellutato, Jr. |
| 2015/0125502 A1 | 5/2015 | Colurciello et al. |
| 2015/0336788 A1 | 11/2015 | Vellutato, Jr. et al. |
| 2016/0120379 A1 | 5/2016 | Balestri |
| 2017/0021973 A1 | 1/2017 | Bray |
| 2017/0036822 A1 | 2/2017 | Sam |
| 2017/0291054 A1 | 10/2017 | Compo et al. |
| 2018/0148228 A1 | 5/2018 | Bray |
| 2018/0148659 A1 | 5/2018 | Mathews |
| 2019/0023477 A1 | 1/2019 | Kelley et al. |
| 2020/0085982 A1 | 3/2020 | Compo |
| 2021/0284424 A1 | 9/2021 | Balestri |
| 2023/0381351 A1 | 11/2023 | Compo |
| 2024/0263107 A1 | 8/2024 | Compo |

FOREIGN PATENT DOCUMENTS

| | | |
|---|---|---|
| CN | 101247838 A | 8/2008 |
| CN | 101559033 A | 10/2009 |
| CN | 203447373 U | 2/2014 |
| CN | 104548224 A | 4/2015 |
| FR | 2 876 358 A1 | 4/2006 |
| GB | 2439059 A | 12/2007 |
| JP | H11501843 A | 2/1999 |
| JP | 2000247808 A | 9/2000 |
| JP | 2002510588 A | 4/2002 |
| JP | 2008086415 A | 4/2008 |
| JP | 2008523233 A | 7/2008 |
| JP | 2013502996 A | 1/2013 |
| JP | 2015199495 A | 11/2015 |
| JP | 2019513465 | 5/2019 |
| KR | 101560582 B1 | 10/2015 |
| WO | 9951509 | 10/1999 |
| WO | 03000170 | 1/2003 |
| WO | 2012141119 A1 | 10/2012 |
| WO | WO-2014/143857 A1 | 9/2014 |
| WO | 2017180306 A1 | 10/2017 |

OTHER PUBLICATIONS

Examination Report for IN Application No. 202117007735, mailed Feb. 25, 2022.
Supplementary European Search Report for EP Application No. 19861884.5, mailed May 3, 2022.
Examination Report for IN Application No. 201817036825, dated May 31, 2021.
International Search Report and Written Opinion for PCT Application No. PCT/US2021/022560, dated Jun. 3, 2021.
Office Action for JP Application No. 2018-553094, dated Jun. 21, 2021.
Willett, Jason, "Finally, a sterile wiper kit for USP<800> compliance!, " WipeDown 1-2-3 Wipe Kit, Mar. 23, 2016, URL: https://www.linkedin.com/pulse/finally-sterile-wiper-kit-usp800-compliance-jason-willett.
Chinese Office Action and Translation of CN Application No. 201780022133.0, dated Mar. 9, 2021, 34 pages.
Examination Report for AU Application No. 2017251631, mailed Feb. 7, 2022.
ExpressWeb EFS 174, Product Definition Sheet, Glenroy, Inc., Nov. 3, 2010, 1 page.
Hypo-Chlor 5.25% Wipe, Safety Data Sheet, Veltek Associates, Inc., vol. 77, No. 58, Mar. 26, 2012, 6 pages.
International Search Report and Written Opinion issued in PCT/US2017/023760 mailed Jun. 15, 2017.
Office Action for JP Application No. 2018-553094, dated Oct. 19, 2020, 7 pages.
Search Report received in SG Application No. 10202003053V, mailed Feb. 8, 2022.
Office Action received in CN Application No. 201780022133.0, mailed Jul. 17, 2020.
International Search Report for EP Application No. EP17782818, dated Oct. 30, 2019, 8 pages.
Office Action received in KR Application No. 10-2018-7030810, mailed Jul. 28, 2021.
International Preliminary Report on Patentability for PCT/US2021/022560, dated Sep. 29, 2022.
Office Action for CN Application No. 202210035688.1, dated Sep. 22, 2022.
Written Opinion for SG Application No. 11202101723S, mailed Oct. 6, 2022.
International Preliminary Report on Patentability for PCT Application No. PCT/US2019/051243, dated Mar. 25, 2021.
Korean Decision to Grant for KR 10-2018-7030810, dated May 26, 2022.
Notice of Grant received in CN Application No. 201780022133.0, mailed Nov. 2, 2021.
Office Action for CA Application No. 3019337, dated Mar. 9, 2023.
Office Action for CN Application No. 201980060483.5, dated Aug. 26, 2022.
Office Action for CN Application No. 201980060483.5, dated Mar. 22, 2022.
Office Action for CN Application No. 202210035688.1, dated Apr. 14, 2023.
Office Action for JP Application No. 2022-046290, dated Feb. 27, 2023.
Office Action for U.S. Appl. No. 17/202,781, dated Mar. 13, 2023.
Office Action for U.S. Appl. No. 17/202,781, dated Sep. 15, 2022.

(56) References Cited

OTHER PUBLICATIONS

Supplementary Search Report received in SG Application No. 10202003053V, dated Mar. 29, 2023.
Office Action for U.S. Appl. No. 17/402,750, dated Jul. 7, 2023.
Office Action for JP Application No. 2021-514370, dated Feb. 13, 2023.
Office Action for JP Application No. 2021-514370, dated Oct. 20, 2023, 11 pages.
Extended European Search Report for EP Application No. EP 21771748.7, mailed Oct. 18, 2023, 6 pages.
Office Action for CA Application No. 3173968, dated Nov. 2, 2023, 4 pages.
Australian Examination Report No. 1 issued in App. No. AU2022241501, dated Nov. 13, 2023, 3 pages.
Patent Examination Report No. 1 issued in App. No. NZ786445, dated Nov. 23, 2023, 4 pages.
Patent Examination Report No. 1 issued in App. No. NZ746838, dated Nov. 23, 2023, 3 pages.
Examination Report for IN Application No. 202117007735, mailed Dec. 13, 2023.
Japanese Office Action (including English translation) issued in App. No. JP2024-022261, dated Apr. 19, 2024, 16 pages.
Willett Jason, "Finally, a sterile wiper kit for USP<800> compliance!", WipeDown 1-2-3. Wipe Kit, (Mar. 23, 2016), p. 1, URL: https://www.linkedin.com/pulse/finally-sterile-wiper-kit- usp 800-compliance, XP055580220.
Chinese Office Action (including English translation) issued in App. No. 202210035688.1, dated Oct. 21, 2024, 22 pages.
European Office Action issued in App. No. 19 861 884.5, dated Dec. 12, 2024, 5 pages.
Japanese Office Action (including English translation) issued in App. No. JP2022555618, dated Aug. 27, 2024, 10 pages.

\* cited by examiner

POUCH WITH BREAKABLE SEAL

RELATED APPLICATIONS

The present application claims the benefit of U.S. Provisional Application No. 62/732,360, filed Sep. 17, 2018, which is hereby incorporated by reference in its entirety into the present disclosure.

FIELD OF THE INVENTION

The invention relates to a wipe kit used for deactivation, decontamination, and disinfection or cleaning in a clean room environment and a method of preparing and using the same.

BACKGROUND OF THE INVENTION

A clean environment or controlled environment is a space designed, maintained, and controlled to prevent particle and microbiological contamination of products. Clean environments include clean rooms and clean workspaces (such as hooded workspaces), which are collectively referred to here as a clean room. Clean rooms are most commonly designed for use in manufacturing facilities and medical research and treatment facilities in the pharmaceutical, biotechnology, and healthcare industries, to name a few. Sterile clean room environments may be classified under a variety of classification schemes, including the International Organization of Standardization ("ISO") Cleanroom Standards, whereby the highest level of sterilization is an ISO 1 clean room and a normal ambient air environment (no sterilization) is classified as ISO 9.

Certain chemical compositions are used inside clean rooms including, for instance, germicidal disinfectants such as phenols, cleaners, quaternary ammonium, peracetic acid, as well as various sporicides, such as peracetic acid, bleach, and hydrogen peroxide. The disinfectants and sporicides are used in clean rooms to disinfect clean room surfaces. In certain clean room environments, such as those in the healthcare industry, surfaces can become exposed to certain hazardous drugs. In those situations, chemicals are needed that can deactivate and decontaminate hazardous drugs on work surfaces to reduce the risk of occupational exposure to technicians and other workers in the clean room, as well as to products or chemicals being prepared in the clean room. The methods of deactivating, decontaminating and disinfecting/cleaning surfaces exposed to hazardous drugs must meet the requirements set forth in USP <800> and USP <797> set forth by the U.S. Pharmacopeial Convention (USP). Conventional methods of clean room sterilization are lacking for this purpose because they do not adequately deactivate the hazardous drugs, but instead simply spread the drug around on the affected surface. On the other hand, products that may be capable of deactivating hazardous drugs are not suitable for use inside of a classified ISO 5 clean room.

Further, the chemical compositions, which are not naturally sterile, need to be sterilized before being able to enter the clean room to avoid risk of contamination. Such compositions can be sterilized by filtration inside of the clean room or can be sterilized before entering the clean room.

To sterilize the compositions outside the clean room, the concentrated composition is either terminally sterilized by irradiation or aseptically processed. To terminally irradiation sterilize the composition, the composition is placed in a container, double bagged, and placed in a lined carton. The entire carton is then terminally sterilized by irradiation. A procedure for terminally irradiation sterilizing a composition is described, for instance, in U.S. Pat. No. 6,123,900 to Vellutato, the disclosure of which is incorporated herein by reference. Some chemicals used in a clean room, however, cannot be irradiated because of their chemical makeup and structure. For example, certain chemicals used to deactivate and decontaminate hazardous drugs in clean rooms cannot be irradiated. This creates problems for introducing such chemicals into a clean room environment and complicates the sterilization process.

Accordingly, the invention is directed to a deactivation wipe kit that improves deactivation, decontamination, and disinfection/cleaning of hazardous drugs from sterile surfaces in a clean room. The deactivation wipe kit of the invention is also able to be irradiated outside of the clean room environment for more efficient transfer and introduction into a clean room.

SUMMARY OF THE INVENTION

It is one aspect of the invention to have a wipe pouch with multiple compartments separated by one or more frangible seals. The wipe pouch can have a first compartment containing a dry wipe, a second compartment having a one-way filling valve coupled thereto, and a coupling assembly (such as a frangible seal) coupling the first compartment to the second compartment. In a closed configuration, the first compartment does not communicate (e.g., air or liquid) with the second compartment. In an opened configuration, the first compartment communicates with the second compartment.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
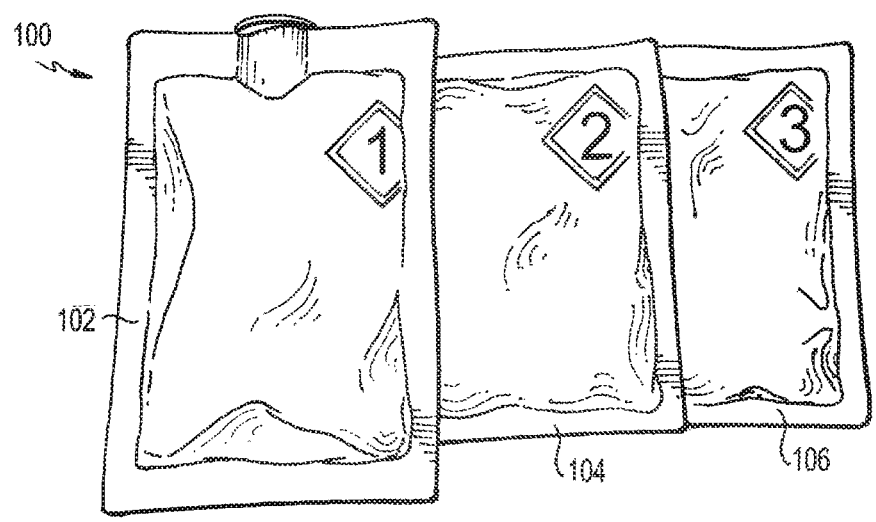
FIG. 1 is a front, perspective view of the deactivation wipe kit according to an embodiment of the invention.

Referring now to FIG. 1, a deactivation wipe kit 100 is illustrated. As used more fully herein, the term "wipe kit" is used to refer to the deactivation wipe kit 100. In one embodiment, the wipe kit 100 includes three pouches 102, 104, 106. Each of these pouches contains a wipe that is saturated in a different chemical used to deactivate and decontaminate hazardous drugs in a clean room environment and disinfect the work surface. In use, the technician applies each wipe from each of the pouches 102, 104, 106 in sequence to a contaminated work surface, such that the wipe in the first pouch 102 is used first, the wipe in the second pouch 104 is used second, and the wipe in the third pouch 106 is used last. When used in this way, the deactivation wipe kit 100 deactivates, decontaminates, and disinfects/cleans most hazardous drugs from work environments for compounding sterile preparations, such as an ISO 5 clean room, as cited by USP <800> and USP <797> set forth by the U.S. Pharmacopeial Convention (USP).

In one embodiment, the first pouch 102 contains a wipe that is saturated in a 5.25% hypochlorite solution, such as sodium hypochlorite (e.g., HYPO-CHLOR® available commercially from Veltek Associates, Inc. of Malvern, PA). This composition is the primary agent that deactivates the hazardous drug(s). It deactivates potentially active drugs that may be present on a compounding surface, and renders the surface safe and decontaminated for future handlers and ensures that the compounding preparations are following USP <797> compounding sterile preparations for patient protection protocol along with USP <800> compliance for hazardous drugs (handling in healthcare settings). While the use of sodium hypochlorite is preferred, any chemical known to deactivate hazardous drugs may be used to saturate the wipe in the first pouch 102, including, but not limited to, potassium permanganate and alkaline potassium permanganate.

The second pouch 104 contains a wipe that is saturated in 2% thiosulfate, such as sodium thiosulfate (e.g., THIO-WIPE™ available commercially from Veltek Associates, Inc). In a preferred embodiment, the thiosultate is USP Grade. This composition is used in order to remove the hypochlorite solution residue from the treated work surface. The thiosulfate renders the hypochlorite, which is a corrosive material, neutral on the surface so as to maintain the surface's structure and integrity. It also functions to decontaminate the work surface. While sodium thiosulfate is preferred, any chemical known to decontaminate a work surface that has been treated with hypochlorite, and which can neutralize the same, may be used. Thus, the sodium thiosulfate solution cleans, decontaminates, and neutralizes the sodium hypochlorite solution and previously deactivated hazardous drugs. It improves the overall longevity of the sterile compounding equipment and stays USP <797> and USP <800> compliant.

The third pouch 106 contains a wipe that is saturated in 70% isopropyl alcohol (IPA) (e.g., ALCOH-WIPE® available commercially from Veltek Associates, Inc.), which functions as a disinfectant. In a preferred embodiment, the IPA is USP Grade. This wipe further cleans and disinfects the treated surface and returns the surface back to its original condition for worker safety. While IPA is preferred, any chemical known to clean and disinfect a work surface may be used, including, but not limited to, sterile water or known germicidal agents such as phenols, quats, peroxyacetic acid (POAA) and $H_2O_2$. Thus, the IPA provides an additional measure against contaminates present on the compounding surfaces for added protection. After deactivation of the work surface, additional disinfection is needed to maintain a critical, controlled, work environment for compounding sterile products.

All three chemicals used in each of the pouches 102, 104, 106 may be formulated with Water for Injection (WFI) and filtered at 0.2 microns. Once a surface is fully treated by all three wipes, the surface can return to its natural composition.

Each of the wipes contained in pouches 102, 104, 106 is preferably formed of a non-woven, non-shedding material that is designed to be clean, have good absorption properties, and provide good surface coverage. The wipe should have good non-shedding properties, as fibers from the wipe should not be easily detached from the wipe so as to avoid contaminating the clean room work surface. In one embodiment, the wipe of the first pouch 102 is formed of 100% polypropylene, while the wipes in the second pouch 104 and third pouch 106 are formed of 100% polyester. In this embodiment, the material of each wipe is chosen for its compatibility with the particular chemical present in each of the pouches 102, 104, 106. Each of these materials produces a fabric-like wipe that is strong, has good non-shedding particulate performance, and is compatible with the chemical in which it is saturated as well as use in a controlled environment. In one embodiment, the wipe is about 9"×12" in size such that it can treat a surface area of approximately six (6) square feet.

In one embodiment, the wipe for the first pouch 102 is a 162XL-4019, 48 gauge polyester with an ALOX coating bonded to 150 (6 mil) white polytheylene. This particular substrate retains the active hypochlorite, though other suitable wipes can be provided. Further, this wipe material minimizes the degradation and instability associated with hypochlorite caused by exposure to organic material. In one embodiment, a single wipe is provided in each pouch 102, 104, 106; however more than one wipe can be provided in any or all of the pouches 102, 104, 106.

Figure 2:
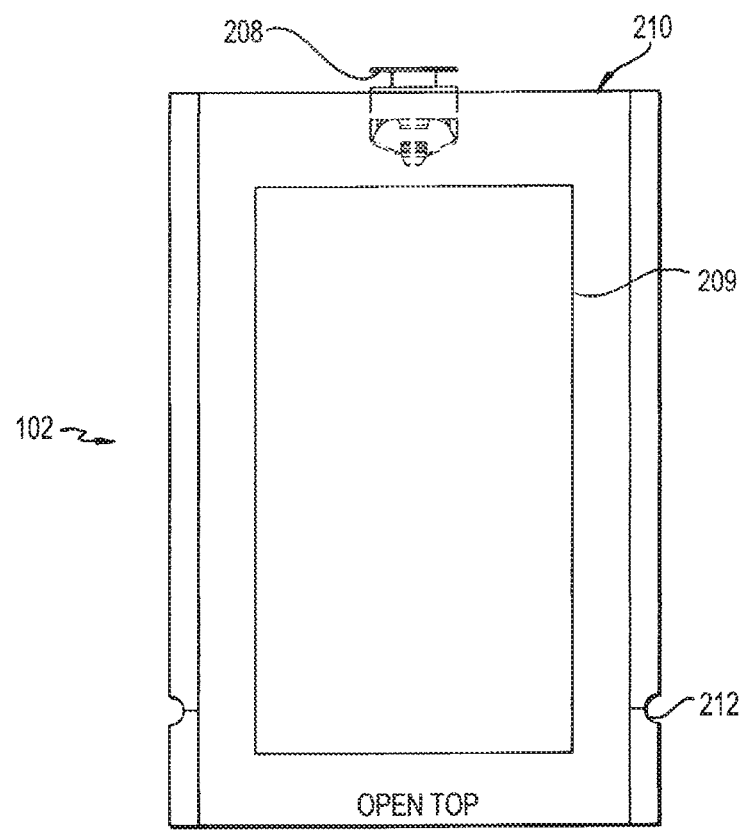
FIG. 2 is a front, plan view of the first pouch of the deactivation wipe kit having a one-way valve according to an embodiment of the invention.
Figure 3A:
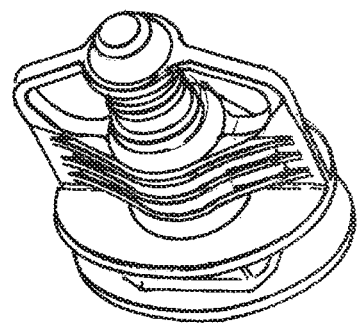
FIGS. 3A-E are perspective views of the one-way valve illustrated in FIG. 2.
Figure 3B:
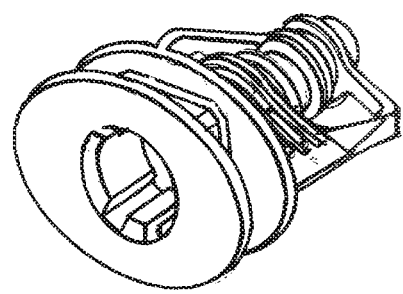
Figure 3C:
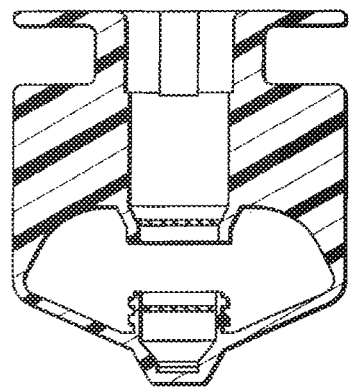
Figure 3D:
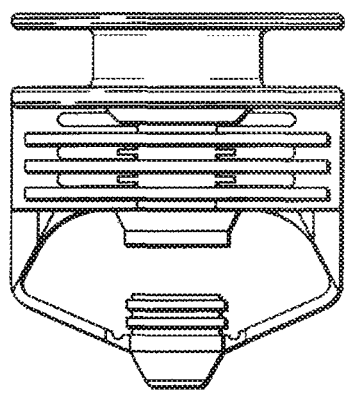
Figure 3E:
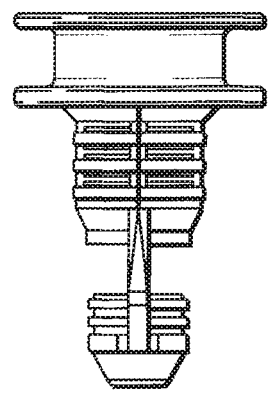

The pouches 102, 104, 106 themselves are designed as flexible packaging structures for the wipes. The pouches 102, 104, 106 are preferably formed of a material that provides a barrier to moisture, air and light and has good chemical resistance so as to maintain its structural integrity during irradiation and when ultimately shelved in the clean room. In one embodiment, each pouch 102, 104, 106 is formed of a multi-layered structure comprised of layers of coated polyester, low density polyethylene, aluminum foil, hydroxypropylcellulose, and/or linear low density polyethylene. For example, the pouches 102, 104, 106 can be ExpressWeb EFS174, by by Glenroy Inc., which is attached hereto and hereby incorporated by reference. When prepared into a multi-layered structure, these materials provide an air-tight and liquid-tight seal and are highly chemically resistant (since stability of the finished product can be affected by light, oxygen and organic matter). They also help to maintain the active agents in each of the chemicals so as to prolong their shelf life. Each of the pouches 102, 104, 106 preferably includes a notch or perforation 212, such as shown in FIG. 2 in the first pouch 102. The notch 212 can be formed in the side of the pouch 102, 104, 106, so that the user can tear open the pouch 102, 104, 106 by pulling on the side of the pouch at the notch 212. Thus in use, the technician pulls the pouch along the perforation in order to tear the pouch 102, 104, 106 open to access the saturated wipe contained therein.

In order to introduce the deactivation wipe kit 100 into the clean room, it (and its contents) must first be sterilized. In one embodiment, parts of the deactivation wipe kit 100 is irradiated to avoid introducing contaminants into the environment. The second pouch 104 and third pouch 106 contain chemicals that may be terminally irradiation sterilized, such as by the methods described herein. Thus, assembled pouches 104, 106 may undergo known terminally irradiation sterilization. The first pouch 102, however, contains a chemical (i.e., sodium hypochlorite) that cannot be terminally irradiation sterilized. As such, the first pouch 102 is configured differently than the second pouch 104 and third pouch 106 such that the chemical can be added after the first pouch 102 has been sterilized.

As set forth in FIG. 2, the first pouch 102 is designed with a one-way valve 208 positioned at an end 210 thereof, and the pouch 102 contains a wipe 209. This valve 208, which is more fully illustrated in FIGS. 3A-E, only allows fluids to be transferred through it in one direction. As such, the first pouch 102, containing only a dry wipe, may be terminally irradiation sterilized, together with the second pouch 104 and third pouch 106 (each of which contain the wipe and the respective chemical). Then, when the pouches 102, 104, 106 are transferred to the clean room, the first pouch 102 may be aseptically filled with the sterilized hypochlorite solution via the one-way valve 208 to saturate the dry wipe contained therein. The sterilized hypochlorite solution may be of any concentration determined suitable to one or ordinary skill in the art. For example, a hypochlorite concentration of 5.25% is used. At this point, the deactivation wipe kit 100 is fully ready for use in a clean room. The wipes contemplated for the kit may be of any conventional size known in the art, exemplarily 3"×4", 4"×6", 9"×9", 9"×12", or 12"×12".

Figure 4:
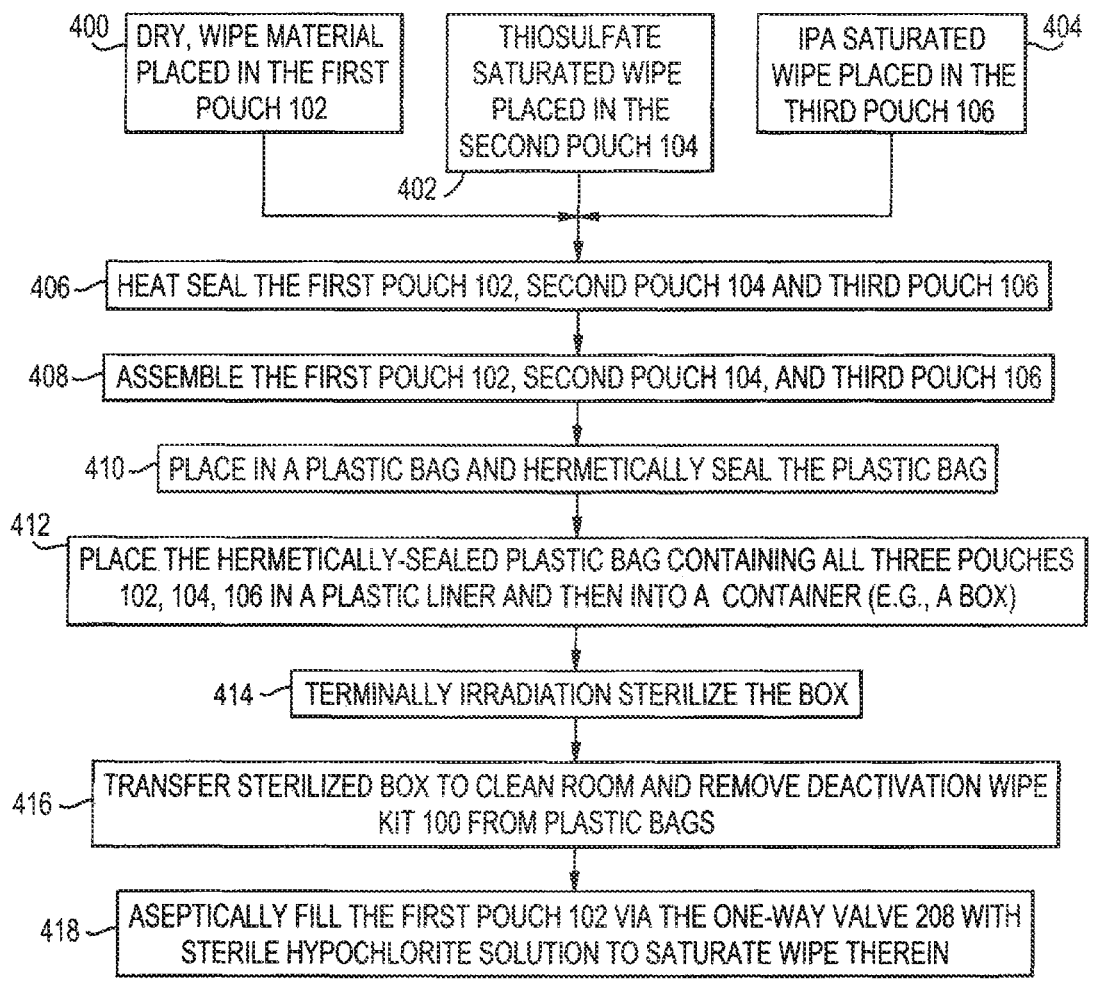
FIG. 4 is a flowchart outlining the steps of a method of preparing a deactivation wipe kit according to an embodiment of the invention.

A process of preparing the deactivation wipe kit 100 is outlined in the flow chart of FIG. 4. Each pouch 102, 104, 106 may be prepared in sequence or simultaneously by different technicians. Thus, Steps 400, 402, 404 can be performed sequentially or at the same time. As set forth more fully below, each of the steps utilizes the chemicals and materials described above.

In Step 400, a dry, wipe material is placed in the first pouch 102 and hermetically sealed to form a first closed or sealed container or pouch. At this step, there are no chemicals present in the first pouch 102. A wipe saturated with a first solution, such as for example thiosulfate solution (e.g., THIO-WIPE™), is placed in the second pouch 104 and hermetically sealed to form a second closed or sealed container or pouch, Step 402. A wipe saturated with a second solution, such as for example 70% IPA (by concentration) (e.g., ALCOH-WIPE®), is placed in the third pouch 106 and hermetically sealed to form a third closed or sealed container or pouch, Step 404. Each of the pouches 102, 104, 106 is hermetically sealed, Step 406, to enclose the contents of each pouch. In one embodiment, the hermetic seal is a liquid and air tight seal of the pouches 102, 104, 106, such as for example a heat seal. Though the heat sealing, Step 406, is shown as a separate step, it can be part of each of the filling processes of Steps 400, 402, 404.

Each of the first, second and third sealed pouches 102, 104, 106 are assembled in preparation for irradiation sterilization, Step 408. One of each of the first, second, and third sealed pouches 102, 104, 106 are assembled together and placed in a first container such as a first plastic bag and the first plastic bag is then hermetically sealed to form a first closed or sealed pouch enclosure, Step 410. Optionally, the first sealed pouch enclosure can be placed in a second container such as a second plastic bag and the second plastic bag is then hermetically sealed to form a second closed or sealed pouch enclosure. In one embodiment, the first and second plastic bags are a polyethylene bag that is heat sealed. The second (or first) sealed pouch enclosure is then placed into a plastic liner bag (e.g., a polyethylene bag) which is closed and placed into a box or other container. The liner is then closed (such as by being knotted or by a fastener (tie)) and the box is closed to form a closed package, Step 412. The box and the enclosed contents are then terminally irradiation sterilized using known techniques and equipment, Step 414, and can be shipped to an irradiator for sterilization, to form a sterilized closed container. The irradiation sterilizes the container and its contents, including the plastic bags, wipes, pouches, solutions.

The irradiated boxes (sterilized closed containers) are then transferred to a clean environment and the sterilized closed pouch enclosure is removed from the plastic liner bag. The sterilized first, second and third sealed pouches are then removed from the inner-most sealed plastic bag, Step 416. At this point, the second sealed pouch 104 and the third sealed pouch 106 are ready for use. However, the first sealed pouch 102 must be filled with the deactivation chemical. In one embodiment, the first sealed pouch 102 is aseptically filled with a sterile hypochlorite solution via the one-way valve 208 inside the clean room, Step 418. At this step, when the first pouch 102 is filled with the solution, the solution is allowed to saturate the dry wipe in the pouch 102, thereby preparing a saturated, hypochlorite wipe. The valve 208 may close automatically by virtue of its design, though other suitable valve designs can be provided.

Once the valve 208 is closed, the first sealed pouch 102 forms a first closed or sealed filled pouch that is then ready for use as well. Optionally, the first sealed filled pouch 102 can be successively hermetically sealed in a first container and optionally then a second container, such as plastic bags to form a first (and second) first filled pouch enclosure. Once the first sealed filled pouch 102 (or first/second filled pouch enclosure) is ready for use, it is matched with one of the irradiated second sealed pouch 104 and one of the irradiated third sealed pouch 106, to form the deactivation wipe kit 100. Optionally, the deactivation wipe kits 100 can be successively hermetically heat sealed in a first container (e.g., a polyethylene bag) and optionally then a second container (e.g., a polyethylene bag), such as plastic bags. Multiple wipe kits 100 are then placed together into a carton having a plastic liner. The plastic liner can be closed (such as by being knotted or by a fastener (tie)) and the box is closed to form the final closed package. The box can then be shipped to the customer for use.

Alternate processes of preparing the deactivation wipe kit 100 may also be performed. The drying, wiping, and placement of material in the first pouch 102 (Step 400) may be performed before, during, or after the placement of the thiosulfate-saturated wipe in the second pouch 104 (Step 402), and before, during or after the IPA-saturated wipe is placed in the third pouch 106 (Step 404). Similarly, the placement of the thiosulfate-saturated wipe in the second pouch 104 (Step 402) and the placement of the IPA-saturated wipe in the third pouch 106 (Step 404) may occur in any order relative to the preparation of the other pouches, as long as all three pouches 102, 104, and 106 can be prepared prior to the step of heat sealing, if packaged together in a same box. However, the irradiated second and third pouches can be packaged together in a box separate from the first final pouch.

In addition it will further be appreciated that other suitable techniques can be utilized to irradiation sterilize the pouches 102, 104, 106. For instance, the multiple pouches 102, 104, and/or 106 can be heat sealed in the same or different individual first (and optionally second) plastic bags. In one embodiment, each closed pouch 102, 104, 106 can be individually single/double bagged (i.e., heat sealed in a first plastic bag (and optionally a successive second plastic bag) to form respective first and second sealed enclosures for the first, second and third closed pouches), then placed in a carton liner and a box and sterilized. In another embodiment, multiple first closed pouches 102 can be heat sealed together in a first bag to form a first enclosure, multiple second closed pouches 104 can be heat sealed in a second bag to form a second enclosure, and multiple third closed pouches 106 can be heat sealed in a third bag to form a third enclosure; and the first, second and third enclosures can be placed in a liner and box and simultaneously irradiated.

Still further, multiple first closed pouches 102 can individually be single/double bagged and placed into a first box; multiple second closed pouches 104 can individually be single/double bagged and placed into a second box; and multiple third pouches 106 can individually be single/double bagged and placed into a third box. Or, multiple first sealed pouch enclosures can be placed in a first box for irradiation, and multiple second and third pouch enclosures can be placed together in a second box for irradiation. In addition, the first and second containers can be any suitable containers such as pouches, and the first, second and third pouches 102, 104, 106 can be any suitable container.

Figure 5:
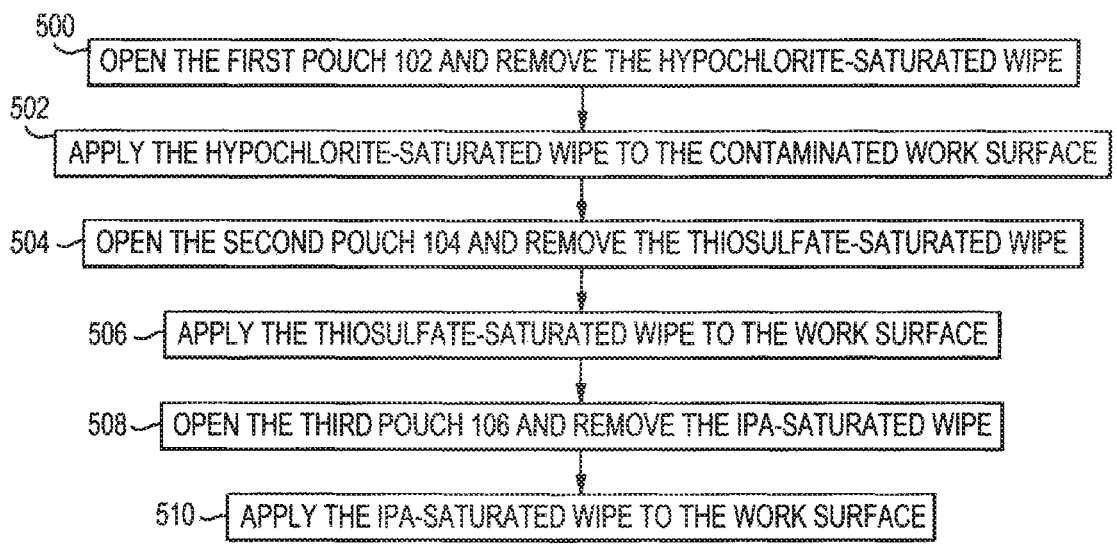
FIG. 5 is a flowchart outlining the steps of a method of using the deactivation wipe kit according to an embodiment of the invention.

Thus, an end user can receive a single box having multiple kits, each kit having a first, second and third sterilized closed pouch. A method of using the deactivation wipe kit 100 is outlined in FIG. 5. Once the box arrives at the customer, the box and box liner are opened (e.g., in a clean room or staging area). A kit 100 can then be removed from the box for use, and brought into the clean room. The heat sealed bag is opened and the pouches 102, 104, 106 are removed. As set forth in Step 500, the first pouch 102 is opened (e.g., by tearing the perforation 212) and the hypochlorite-saturated wipe is removed. The wipe is then applied to the contaminated work surface in order to deactivate the hazardous drug(s), Step 502. Next, the second pouch 104 is opened and the thiosulfate-saturated wipe is removed, Step 504. The wipe is then applied to the work surface that has just been treated with the hypochlorite-saturated wipe, Step 506, in order to decontaminate the surface and remove any hypochlorite residue that may still be present on the surface. The third pouch 106 is then opened and the IPA-saturated wipe is removed, Step 508. Lastly, the wipe is applied to the work surface in order to disinfect and clean the surface to render it safe for use by a technician or worker, Step 510. Once each wipe is used consecutively on the surface, any hazardous drugs that are present are deactivated and decontaminated and the surface is disinfected and safe for use by the technician.

Thus, multiple variations of the invention are apparent within the scope of the present invention. The first, second and third pouches can be individually single/double-bagged (i.e., hermetically sealed in a first pouch and successive second pouch). Or the second and third pouches can be single/double-bagged together for irradiation and delivery to the end user; and either matched in a box with a double-bagged first filled pouch enclosure or boxed separately from the single/double-bagged first filled pouch enclosure. Still other variations are possible within the spirit and scope of the invention. For instance, the end user can receive a first box with the first sterilized closed pouches, and a second box with the second and third sterilized closed pouches. In addition, although the invention is described for use with three pouches each having a different solution, other suitable number of pouches and solutions can be provided, such as two or four or more.

Figure 6:
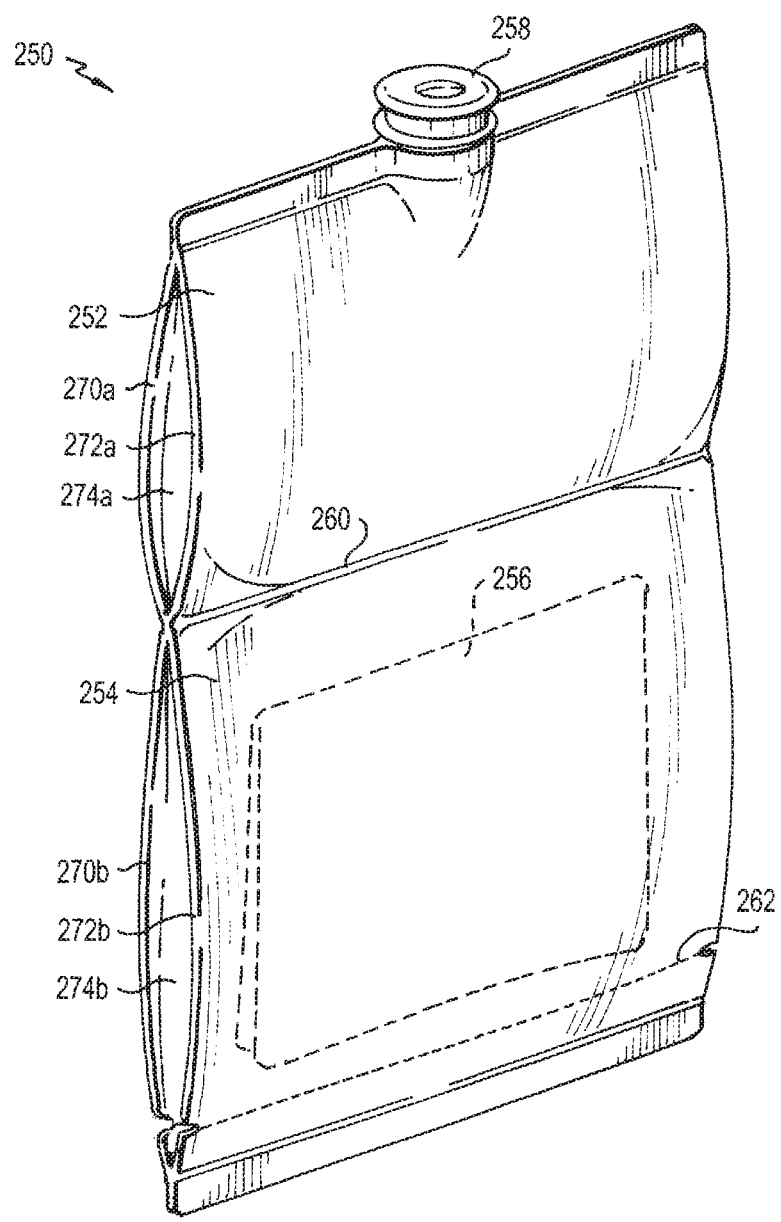
FIG. 6 is a perspective view of a pouch in accordance with another embodiment of the invention, having side walls at the longitudinal sides between the first and second bag layers.
Figure 7:
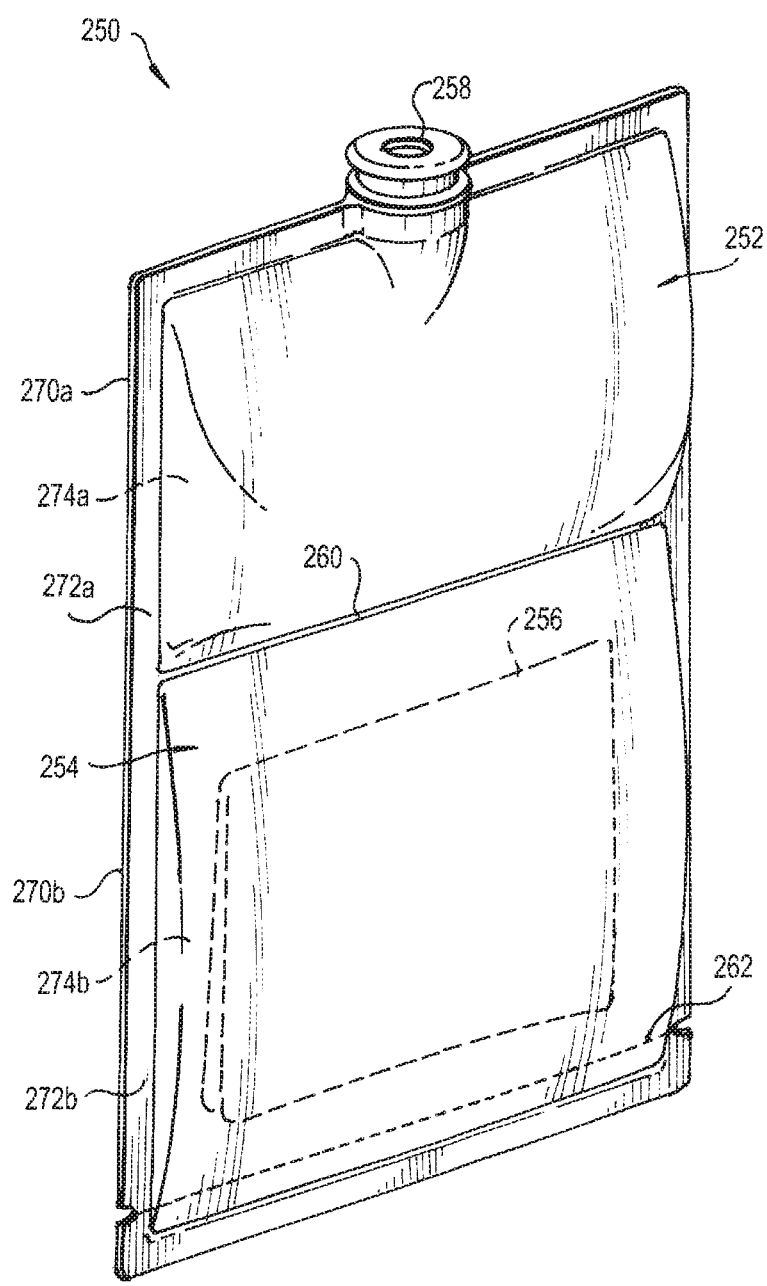
FIG. 7 is a perspective view of a pouch in which the longitudinal and transverse sides of the first and second bag layers are heat sealed directly to one another, without side walls.

For example, a further illustrative non-limiting example of the invention is shown in FIGS. 6, 7. Here, an alternative embodiment for the first pouch 250 is shown. The pouch 250 has two polyethylene layers 270, 272 that are heat sealed at the edges (either directly to one another, FIG. 7, or with a side wall therebetween, FIG. 6) to define an interior space 274 therebetween. The pouch is substantially rectangular in shape with two longitudinal sides and two transverse sides that are substantially orthogonal to the longitudinal sides. A transverse coupling assembly, such as a frangible seal 260, is formed in the center to define a first compartment 252 and a second compartment 254. The first compartment 252 has a first layer 270a, second layer 272a and an interior space 274a therebetween, and the second compartment 254 has a first layer 270a, second layer 272a, and an interior space 274b therebetween. The frangible seal 260 is substantially parallel to the transverse sides and extends the entire width of the pouch 250. The first and second compartments 252, 254 are completely liquid tight so that liquid cannot pass from the first compartment 252 to the second compartment 254, or vice versa.

In operation, the pouch 250 is formed by heat sealing the layers 270, 272 along their two longitudinal sides (either directly to one another, FIG. 7, or with a side wall therebetween, FIG. 6), and then applying the frangible heat seal 260. A dry wiper 256 is then placed in the interior space 274b of the second compartment 254 and the bottom transverse side is heat sealed to fully enclose the wiper 256 in the second compartment 254. A laser score 262 can be formed along at least a portion of the second compartment 254, here shown extending transversely across the entire width of the pouch 250. In addition, a valve 258 is placed at the top transverse side, and the entire top transverse side of the two layers 270, 272 is heat sealed to engage the valve 258 at the top of the first compartment 252. The entire pouch 250 is then sterilized by irradiation.

At this point, a liquid is filled into the interior space of the first compartment 252 via the valve 258. In one embodiment, the liquid is a disinfectant such as a bleach, which is filtered and aseptically filled inside a clean room into the first compartment 252. The pouch 250 is then packaged for delivery to a clean room for use, such as by being successively double bagged in two polyethylene bags and placed in a plastic liner and then a cardboard box for delivery.

The frangible seal 260 is weaker than the outer perimeter heat seals. The frangible seal 260 can be formed, for instance, by bonding at a lower heat. When the wiper 256 is ready for use, the user opens the outer packages. The user then presses on the first and/or second compartments 252, 254, which breaks the frangible seal 260. The interior space 274a, 274b of the first and second compartments 252, 254 are then in liquid communication with one another, whereby breaking the seal 260 releases the liquid from the first compartment 252 to come into contact with the wiper(s) 256 in the second compartment. The frangible seal 260 does not weaken the outer plastic layers forming the pouch 250, so that the pouch 250 is liquid-proof and no liquid escapes out of the pouch 250. Once the liquid has been absorbed by the wiper 256, the user opens the second compartment 254 along the laser score 262. The user then removes the wet wiper 256 from the interior space 274, for use in the clean room.

In this manner, the liquid does not come into contact with the wiper 256 until just prior to the wiper 256 being used, which can be important where the liquid (such as a bleach) can otherwise degrade the wiper 256. That extends the shelf life of the product. It is further noted that the pouch 250 can be formed in any suitable manner, though the frangible heat seal 260, score 262 and two longitudinal seals can be made prior to introducing the wiper 256 so that the wiper 256 does not inadvertently get caught in or otherwise damaged by any of those operations. However, in another embodiment, the bottom transverse side and the two longitudinal sides can be heat sealed. The wiper 256 can then be placed inside the pouch 250 and the frangible heat seal 260 and top transverse heat seals applied. In another embodiment of the invention, the wiper 256 can be placed between the two layers 270, 272, then all of the seals formed at the same time, including the frangible seal 260 and the heat seals along the longitudinal sides and at the top and bottom transverse sides.

The dual compartment 252, 254 pouch 250 of FIG. 6 can be used with the second pouch 104 and third pouch 106 in the systems and methods described with respect to FIGS. 1-5. For example, the pouch 250 with the dry wiper 256 can be irradiated together with the second pouch 104 and third pouch 106. However, the dual compartment pouch 250 of FIG. 6 also has separate utility by itself, and can be used in other suitable applications, and need not be used with the second and third pouches 104, 106. For example, the pouch 250 can be used by itself when only a single wiper is needed.

It is further noted that the invention is shown and described as a pouch 250 having two compartments 252, 254 separated by a frangible seal 260. The two compartments 252, 254 are directly attached to each other and separated by the frangible seal 260, so that the compartments 252, 254 are in liquid communication with one another when the seal 260 is opened. It should be noted that the two compartments can be placed in communication with one another in other manners without using a frangible seal, within the spirit and scope of the invention, such as for example by using a valve or other connection device or coupling assembly.

In addition, it is noted that the frangible seal 260 is shown extending the entire width of the pouch 250. It is noted that the frangible seal 260 need not extend the entire width. For example, part of the seal 260 can be a full heat seal that permanently separates the first compartment 252 from the second compartment 254, and part of the seal 260 can be a frangible seal that can be opened to release liquid from the first compartment 252 into the second compartment 254.

Still further, as shown in FIG. 7, the frangible seal 260 seals the first layer 270 directly to the second layer 272, which are flat, so that the two layers 270, 272 come together at the seal. Thus, the first layer 270 is sealed directly to the second layer 272 without any other material positioned therebetween. In this manner, the seal 260 forms a tapered area between the first and second compartments 252, 254. The seal 260 can have any suitable thickness, either small to form a line or pinch point, or wide to form a flattened area. In one embodiment, the seal 260 can have a thickness of about 0.3125 inches, the first compartment can have a length of about 5.3125 inches, the second compartment can have a length of about 6.375 inches, and the pouch can have a width of about 4.5 inches and a total length of about 12 inches. The first compartment can hold approximately 30 mL of liquid or solution, and the second compartment can hold one or more folded 12×12 knitted wipers. In addition, the seal 260 need not be linear, as shown, but can have other shapes such as curved. In another embodiment of the invention, the first compartment 252 can be the same size as the second compartment 254, or a different size, either smaller or larger than the second compartment 254. The first and second compartments can be generally square or rectangular, or other suitable sizes and shapes.

In still a further embodiment, additional transverse frangible seals can be provided to define more than two liquid-tight compartments in the pouch. For example, a first compartment containing a first product (e.g., dry wipe), liquid or substance; a second compartment containing a second product, liquid or substance, and a third compartment containing a third product, liquid or substance. The compartments can be arranged so that they all communicate with each other when the frangible seals are broken, or that the second compartment is positioned between the first and second compartments, so that the first and third compartments only communicate with the second compartment. And, the frangible seals can have different breaking points or separately broken, so that, for example, a first frangible seal can be broken to release the content from a first compartment into a second compartment, then a second frangible seal can be broken to release the contents from the first and second compartments into the third compartment.

As noted, FIG. 7 shows that the longitudinal sides of the first and second layers 270, 272 are directly heat sealed to one another. And FIG. 6 shows that the pouch 250 can have side walls that extend between the longitudinal sides of the first layer 270 and the second layer 272, for the first compartment 252 and/or the second compartment 254. The side walls allow the layers 270, 272 to separate at the longitudinal sides so that they can retain more liquid, substance or product in the compartments 252, 254. The side walls are heat sealed to the first and second layers 270, 272. For example, the side wall can be substantially rectangular and tapered to a point or oblong, with a first longitudinal side that couples to the first layer 270 and a second longitudinal side that couples to the second layer 272. There can be one side at each longitudinal side of the pouch 250, that gets sealed in the middle by the frangible seal 260, or two longitudinal sides, one for the first compartment 252 and one for the second compartment 254. In operation, the sides can be heat sealed to the layers 270, 272 in a single heat-sealing operation that applies a heat seal to each longitudinal side of the side wall, or two heat-sealing operations, one that applies a heat seal to the first longitudinal side and a second that applies a heat seal to the second longitudinal side.

Finally, it is noted that the description and claims use several geometric or relational terms, such as parallel, linear, curved, rectangular, perpendicular, and flat. In addition, the description and claims use several directional or positioning terms and the like, such as top, bottom, sides, longitudinal, transverse, and interior. Those terms are merely for convenience to facilitate the description based on the embodiments shown in the figures. Those terms are not intended to limit the invention. Thus, it should be recognized that the invention can be described in other ways without those geometric, relational, directional or positioning terms. In addition, the geometric or relational terms may not be exact. For instance, walls may not be exactly perpendicular or parallel to one another but still be considered to be substantially perpendicular or parallel because of, for example, roughness of surfaces, tolerances allowed in manufacturing, etc. And, other suitable geometries and relationships can be provided without departing from the spirit and scope of the invention.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is claimed:

1. A hazardous drug deactivation wipe kit, comprising:
a first pouch having an automatically closing one-way fill valve coupled to an end thereof, the first pouch having a first compartment containing a dry wipe, a second compartment having a disinfectant filled to said second compartment through said one-way fill valve, and a heat seal formed between the first compartment and the second compartment, said first pouch having a flexible outermost layer with an access having a closed position that denies access to the dry wipe in said first compartment, and an open position that permits access to the dry wipe in said first compartment;
a second pouch containing a wipe saturated in thiosulfate solution; and
a third pouch containing a wipe saturated in isopropyl alcohol solution,
wherein the deactivation wipe kit is configured for use in a controlled environment to deactivate hazardous drugs on a work surface.

2. The deactivation wipe kit of claim 1, wherein the disinfectant comprises a hypochlorite solution that is a 5.25% sodium hypochlorite solution.

3. The deactivation wipe kit of claim 1, wherein the thiosulfate solution is a 2% sodium thiosulfate solution.

4. The deactivation wipe kit of claim 1, wherein the isopropyl alcohol solution is a 70% isopropyl alcohol solution.

5. The deactivation wipe kit of claim 1, wherein the wipe in the first pouch is formed of 100% polypropylene.

6. The deactivation wipe kit of claim 1, wherein the wipe in the second pouch and the wipe in the third pouch is formed of 100% polyester.

7. The deactivation wipe kit of claim 1, wherein each of the first pouch, the second pouch, and the third pouch are formed of a multi-layered structure comprised of materials selected from the group consisting of coated polyester, low density polyethylene, aluminum foil, hydroxypropylcellulose, linear low density polyethylene, and combinations thereof.

8. The deactivation wipe kit of claim 1, wherein each of the first pouch, the second pouch, and the third pouch comprise a perforation adjacent to an end thereof.

9. The deactivation wipe kit of claim 1, wherein the one-way fill valve is configured to permit the first pouch to be filled into the first compartment with the hypochlorite solution through the one-way fill valve after the wipe has already been sealed in the first compartment, said one-way fill valve automatically closes to prevent the hypochlorite solution from escaping through said one-way fill valve.

10. A method of preparing a deactivation wipe kit, comprising the steps of:
(a) placing a dry wipe in a first compartment of a first pouch having an automatic closing one-way fill valve coupled to an end of a second compartment of the first pouch;
(b) placing a thiosulfate-saturated wipe in a second pouch;
(c) placing an isopropyl alcohol-saturated wipe in a third pouch;
(d) hermetically sealing the first pouch, the second pouch, and the third pouch to respectively form a first closed pouch, second closed pouch and third closed pouch;
(e) placing the first closed pouch, the second closed pouch and the third closed pouch in a plastic bag and hermetically sealing the plastic bag to form a closed pouch enclosure;
(f) placing the closed pouch enclosure in a container and irradiation sterilizing the container and its contents to form a sterilized closed container;
(g) transferring the sterilized closed container to a controlled environment and removing the first closed pouch, the second closed pouch, and third closed pouch from the closed pouch enclosure;
(h) aseptically filling the second compartment of the first closed pouch with sterile hypochlorite solution via the one-way valve to saturate the dry wipe with hypochlorite solution.

11. The method of preparing a deactivation wipe kit according to claim 10, wherein step (d) and/or step (e) are performed by heat sealing the first pouch, the second pouch, the third pouch and/or the plastic bag.

12. The method of preparing a deactivation wipe kit according to claim 10, wherein steps (a)-(c) may be formed sequentially or simultaneously.

13. The method of preparing a deactivation wipe kit according to claim 10, wherein the step (e) further comprising placing the first closed pouch, the second closed pouch, and the third closed pouch in a first plastic bag and hermetically sealing the first plastic bag to form a first closed pouch enclosure, and placing the first closed pouch enclosure in a second plastic bag to form a second closed pouch enclosure.

14. The method of preparing a deactivation wipe kit according to claim 10, wherein step (h) forms a first closed filled pouch, and further comprising the step of placing the first closed filled pouch, the second closed pouch and the third closed pouch in a final plastic bag and hermetically sealing the final plastic bag to form a final closed pouch enclosure.

15. The method of preparing a deactivation wipe kit according to claim 14, further comprising the step of placing the final closed pouch enclosure in a liner and a container.

16. The method of preparing a deactivation wipe kit according to claim 10, wherein said step of irradiation sterilizing sterilizes the first pouch, second pouch, third pouch, dry wipe, thiosulfate-saturated wipe, isopropyl alcohol-saturated wipe, plastic bag, and container.

17. A method of using the deactivation wipe kit according to claim 10, comprising the steps of:
(a) removing the wipe from the first pouch and applying the wipe to a work surface contaminated with at least one hazardous drug;
(b) removing the wipe from the second pouch and applying the wipe to the work surface;
(c) removing the wipe from the third pouch and applying the wipe to the work surface,
wherein step (a) deactivates the hazardous drug, step (b) decontaminates the work surface, and step (c) disinfects and cleans the work surface.

18. The method of claim 17, wherein steps (a)-(c) are performed in sequential order.

19. The method of claim 17, wherein each of the wipes are removed from the first pouch, the second pouch, and the third pouch, respectively, by tearing a perforation in each of the first pouch, the second pouch, and the third pouch.

20. The hazardous drug deactivation wipe kit of claim 1, wherein the heat seal is formed by heat sealing.

21. The hazardous drug deactivation wipe kit of claim 20, further comprising a further heat seal at a perimeter formed by the first, second and third pouches, said further heat seal formed by a higher temperature heat sealing.

22. The hazardous drug deactivation wipe kit of claim 1, wherein the first pouch has side walls that extend between the longitudinal sides of a first layer and a second layer of said first pouch, said first layer forming the flexible outermost layer.

23. The wipe kit of claim 1, said first pouch forming a wipe dispenser, and said flexible outermost layer forming an outermost portion of said wipe dispenser.

* * * * *